United States Patent
Kumar et al.

(10) Patent No.: US 10,822,346 B2
(45) Date of Patent: Nov. 3, 2020

(54) MEGLUMINE SALTS OF THIENOPYRIMIDINES

(71) Applicant: Cardurion Pharmaceuticals, LLC, Boston, MA (US)

(72) Inventors: Anuj K. Kumar, Belmont, MA (US); Raymond E. Forslund, Natick, MA (US)

(73) Assignee: CARDURION PHARMACEUTICALS, LLC, Boston, MA (US)

(*) Notice: Subject to any disclaimer, the term of this patent is extended or adjusted under 35 U.S.C. 154(b) by 0 days.

(21) Appl. No.: 16/385,748

(22) Filed: Apr. 16, 2019

(65) Prior Publication Data

US 2019/0315765 A1 Oct. 17, 2019

Related U.S. Application Data

(60) Provisional application No. 62/658,683, filed on Apr. 17, 2018.

(51) Int. Cl.
*C07D 495/04* (2006.01)
*C07C 215/40* (2006.01)

(52) U.S. Cl.
CPC .......... *C07D 495/04* (2013.01); *C07C 215/40* (2013.01)

(58) Field of Classification Search
CPC .................................................. C07D 495/04
See application file for complete search history.

(56) References Cited

U.S. PATENT DOCUMENTS

| | | | |
|---|---|---|---|
| 4,377,583 A | | 3/1983 | Larsen et al. |
| 5,124,331 A | * | 6/1992 | Arita ..................... C07D 495/04 514/232.8 |
| 7,199,151 B2 | | 4/2007 | Shashoua et al. |
| 8,293,754 B2 | | 10/2012 | Gotanda et al. |
| 8,314,077 B2 | | 11/2012 | Webb et al. |
| 8,748,437 B2 | * | 6/2014 | Hayashi ................ C07D 495/04 514/260.1 |
| 2008/0009498 A1 | | 1/2008 | Garvey et al. |
| 2008/0076758 A1 | | 3/2008 | Folkes et al. |
| 2009/0203703 A1 | * | 8/2009 | Gotanda ................ A61P 25/28 514/249 |
| 2011/0275762 A1 | | 11/2011 | Cmiljanovic et al. |
| 2019/0211028 A1 | * | 7/2019 | Mendelsohn .......... A61K 45/06 |

OTHER PUBLICATIONS

Notification of Transmittal of the International Search Report and the Written Opinion of the International Searching Authority, or the Declaration issued in International Application No. PCT/US2019/027665 dated Jun. 13, 2019, 7 pages.
Notification of Transmittal of the International Search Report and the Written Opinion of the International Searching Authority, or the Declaration issued in International Application No. PCT/US17/41249 dated Sep. 26, 2017, 10 pages.
Celanire, S., et al. "Small Molecule Therapeutics for Schizophrenia", Springer, Oct. 13, 2014, p. 292.
Abdel-Megid et al. (2018) "Chemistry of Thienopyrimidines and Their Biological Applications," J. Pharm. Appl Chem. 2(3); 103-107.
Blanton et al. (2012) "Protein Kinase G Ia Inhibits pressure overload-induced cardiac remodeling and is required for the cardioprotective effect of aildenafil in vivo." Journal of the American Heart Association, 5(a003731):1-10.
Braunwald (2015) "The war against heart failure: the Lancet lecture," The Lancet 385 (9970):812-824.
Center for Disease Control (Jun. 16, 2016) "Heart Failure Fact Sheet," U.S. Department of Health and Human Services, 2 pages. Accessible on the Internet at URL: https://www.cdc.gov/dhdap/data statistics/fact sheets/fs heart failure.htm.
Takimoto et al. (2005) "Chronic Inhibition of cyclic GMP phosphodiesterase 5A prevents and reverses cardiac hypertrophy." Nature Medicine. 11(2):214-222.

* cited by examiner

*Primary Examiner* — D Margaret M Seaman
(74) *Attorney, Agent, or Firm* — Mintz, Levin, Cohn, Ferris, Glovsky and Popeo, P.C.

(57) ABSTRACT

Disclosed herein are thienopyrimidine meglumine salts according to Formula (I) used for treating or preventing heart failure:

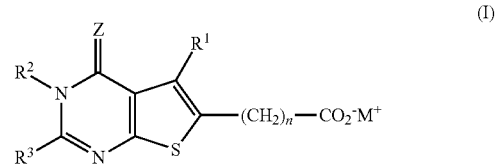

(I)

21 Claims, 2 Drawing Sheets

MEGLUMINE SALTS OF THIENOPYRIMIDINES

CROSS REFERENCE

This application claims the benefit of priority to U.S. provisional application No. 62/658,683, filed on Apr. 17, 2018, which is incorporated herein by reference in its entirety.

FIELD

The present invention relates to thienopyrimidine meglumine salts used for treating or preventing heart failure.

BACKGROUND

Heart failure is a global problem affecting 38 million patients worldwide and is the most common diagnosis in hospitalized patients aged 65 years or older and afflicts more than six million Americans. The 5-year survival rate for heart failure is worse than most cancers with the annual cost of care for heart failure in the USA estimated to exceed 30 billion (USD). Braunwald, Lancet, 385, 812-24 (2015).

In the United States, about 1 million heart failure hospital admissions occur annually. About 5.7 million adults in the United States have heart failure and about half of the people who develop heart failure die within 5 years of diagnosis. Heart failure fact sheet, Center for Disease Control, http://www.cdc.gov/dhdsp/data_statistics/fact_sheets/fs_heart_failure.htm.

In heart failure with reduced ejection fraction (HFrEF), also known as systolic HF, the heart muscle is not able to contract adequately and, therefore, ejects less oxygen-rich blood into the circulation. Patients with this form of the disease will have lower-than-normal left ventricular ejection fraction on an echocardiogram. Heart failure with preserved ejection fraction (HFpEF) is a second type of heart failure that lacks any therapies at present and is thus particularly problematic. HFpEF constitutes at least half of all heart failure cases. Exercise intolerance, pulmonary congestion and fatigue are notable HFpEF symptoms and result in a poor life quality.

Medical care for heart failure includes a number of nonpharmacologic, pharmacologic, and invasive strategies to treat and prevent further deterioration. Phosphodiesterase 9 (PDE9) inhibitors have been previously studied as potential therapeutics for the treatment of diseases such as overactive bladder syndrome, pollakiuria, urinary incontinence, dysuria associated with prostatic hyperplasia, urolithiasis, Alzheimer's disease, chronic obstructive pulmonary disease, myocardial infarction, thrombosis, diabetes and the like. See, e.g., U.S. Pat. No. 8,293,754.

It was recently discovered that thienopyrimidine compounds that inhibit PDE9 have shown promising results in the treatment of cardiovascular diseases and more specifically in the prophylactic treatment of HF. See International Publication no. WO 2018/009899. While thienopyrimidine compounds have shown promising inhibitory effects, the compounds themselves have low solubility due to the free acid. Similarly, forms such as the sodium and potassium salts of thienopyrimidines carboxylates have also demonstrated poor physicochemical properties. See U.S. Pat. No. 8,293,754 (disclosing examples of thienopyrimidine carboxylic acids). For example, the sodium and potassium salts exhibit many problems such as solid form instability, high hygroscopicity, numerous polymorphs, and high residual solvent retention. There remains an unmet need to identify a suitable form of thienopyrimidines in order to develop pharmaceutical formulations for use in the treatment of HF.

SUMMARY

In one aspect the invention comprises a meglumine salt of thienopyrimidine compounds shown in Formula (I)

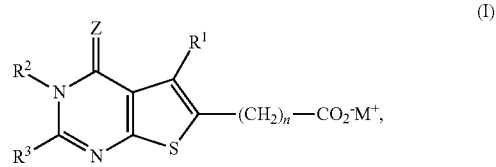

(I)

or stereoisomers, tautomers or hydrates thereof, wherein:

$R^1$ is hydrogen, $(C_1\text{-}C_6)$alkyl, $(C_1\text{-}C_6)$alkoxy or $(C_1\text{-}C_6)$haloalkyl containing 1-6 halogen atoms;

$R^2$ is hydrogen, $(C_1\text{-}C_6)$alkyl, $[(C_1\text{-}C_6)$alkylene]aryl or amino;

$R^3$ is hydrogen, $(C_1\text{-}C_6)$alkyl, $(C_2\text{-}C_6)$alkenyl, $[(C_1\text{-}C_6)$alkylene]N$(R^4)(R^5)$, $[(C_1\text{-}C_6)$alkylene]S$(R^4)$ or —X—Y, or $R^2$ and $R^3$ together with the atoms to which they are attached form a heterocyclyl;

$R^4$ and $R^5$ are independently H or $(C_1\text{-}C_6)$alkyl;

X is a chemical bond, —$CH_2$—, —CH(OH)—, —CH$(C_6H_5)$—, —CO—, —$CH_2CH_2$—, $CH_2CO$—, —$COCH_2$—, S, O or NH;

Y is cycloalkyl, heterocyclyl, aryl or heteroaryl;

Z is S or O;

n is 0, 1, 2, 3 or 4;

$M^+$ is

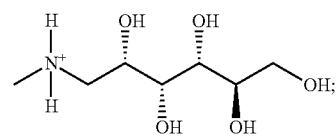

and wherein any alkyl, alkylene, cycloalkyl, heterocyclyl, heteroaryl or aryl is optionally substituted with 1, 2 or 3 groups selected from OH, CN, halogen, $(C_1\text{-}C_6)$alkyl, O$(C_1\text{-}C_6)$alkyl, $(C_2\text{-}C_6)$alkenyl, haloalkyl, amino, oxo and nitro.

In one aspect $R^1$ is $(C_1\text{-}C_6)$alkyl. In another aspect $R^1$ is methyl.

In one aspect $R^2$ is hydrogen.

In one aspect $R^3$ is —X—Y.

In one aspect X is —$CH_2$— and Y is aryl. In another aspect X is —$CH_2$— and Y is a $(C_1\text{-}C_6)$aryl substituted by one or more halogen atoms that are Cl. In yet another aspect X is —$CH_2$— and Y is a phenyl substituted by one or more halogen atoms that are Cl.

In one aspect Z is oxygen.

In one aspect n is 0.

In one aspect of the invention the meglumine salts of Formula (I) are selected from:

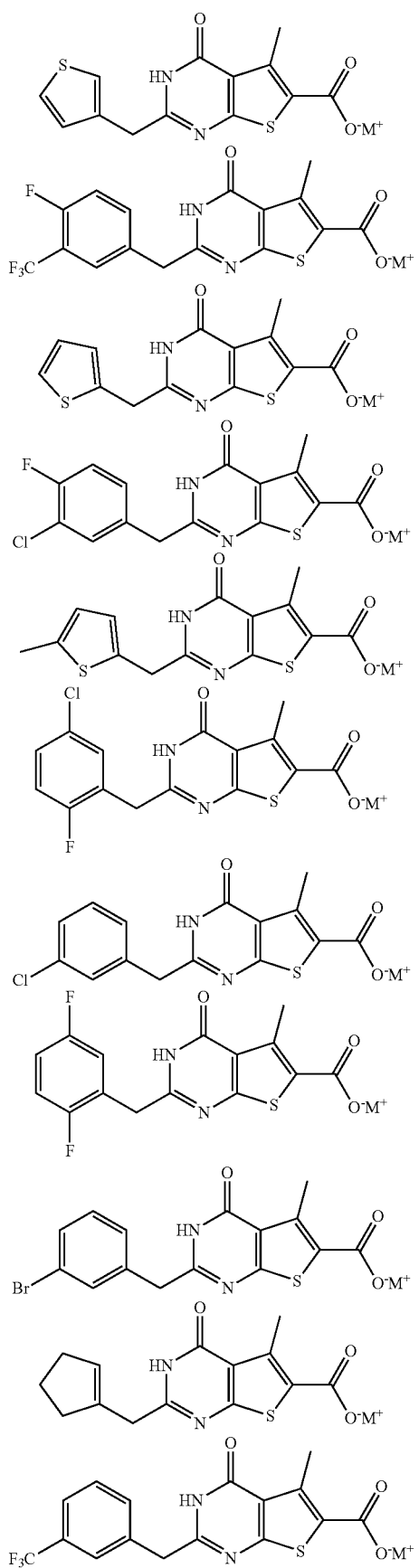
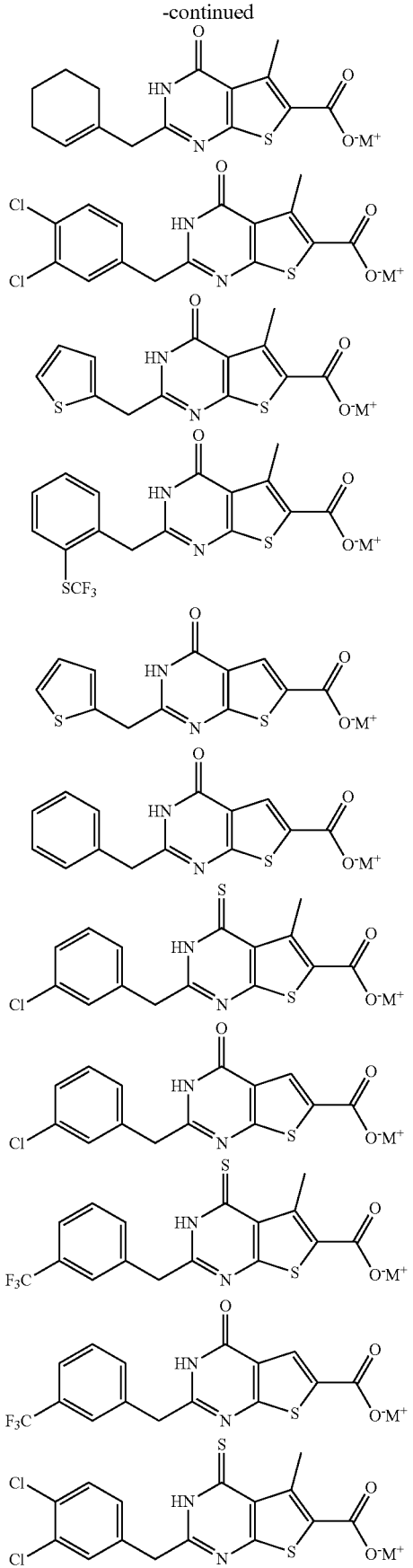

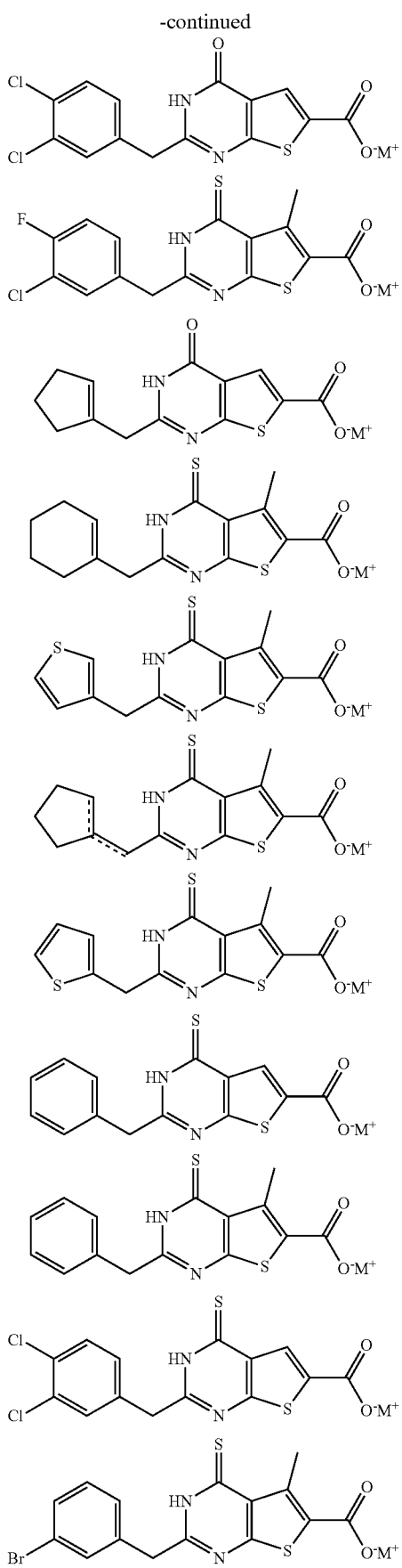

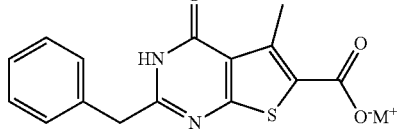

In another aspect the meglumine salts of Formula (I) are selected from:
meglumine 2-(3,4-Dichlorobenzyl)-5-methyl-4-oxo-3,4-dihydrothieno[2,3-d]pyrimidine-6-carboxylate;
meglumine 2-(3-Chlorobenzyl)-5-methyl-4-oxo-3,4-dihydrothieno[2,3-d]pyrimidine-6-carboxylate;
meglumine 5-Methyl-4-oxo-2-(3-trifluoromethylbenzyl)-3,4-dihydrothieno[2,3-d]pyrimidine-6-carboxylate;
meglumine 2-(3-Chloro-4-fluorobenzyl)-5-methyl-4-oxo-3,4-dihydrothieno[2,3-d]pyrimidine-6-carboxylate;
meglumine 2-(5-Chloro-2-fluorobenzyl)-5-methyl-4-oxo-3,4-dihydrothieno[2,3-d]pyrimidine-6-carboxylate;
meglumine 2-(Cyclopent-1-enylmethyl)-5-methyl-4-oxo-3,4-dihydrothieno[2,3-d]pyrimidine-6-carboxylate;
meglumine 4-Oxo-2-(thiophen-2-ylmethyl)-3,4-dihydrothieno[2,3-d]pyrimidine-6-carboxylate;
meglumine 2-Benzyl-4-oxo-3,4-dihydrothieno[2,3-d]pyrimidine-6-carboxylate;
meglumine 2-(3-Chlorobenzyl)-4-oxo-3,4-dihydrothieno[2,3-d]pyrimidine-6-carboxylate; and
meglumine 4-Oxo-2-(3-trifluoromethylbenzyl)-3,4-dihydrothieno-[2,3-d]pyrimidine-6-carboxylate.

In another aspect the meglumine salt of Formula (I) is:

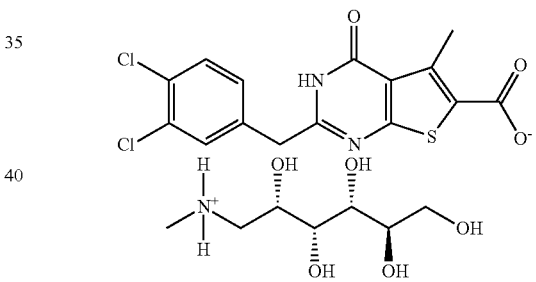

In an aspect of the invention the meglumine salts of Formula (I) are crystalline solids.

In another aspect of the invention the crystalline meglumine salts of Formula (I) are a monohydrate.

In another aspect of the invention the crystalline meglumine salts of Formula (I) are anhydrous.

In another aspect of the invention the crystalline meglumine salt of Formula (I) is a monohydrate having an X-ray powder diffraction pattern with characteristic peaks expressed in values of degrees 2Θ at about 5.24, about 7.53, about 11.40, about 11.62, about 15.04, about 16.77, about 17.58, about 19.54, about 22.18, about 23.33, about 24.38, about 25.90 and about 28.67±0.2.

In an embodiment of the invention the crystalline meglumine salt of Formula (I) is a monohydrate having an X-ray powder diffraction pattern with characteristic peaks expressed in values of degrees 2Θ at about 5.24, about 7.53, about 11.40, about 15.04, about 16.77, about 17.58, about 19.54, about 22.18, about 25.90 and about 28.67±0.2.

In another embodiment of the invention the crystalline meglumine salt of Formula (I) is a monohydrate having an X-ray powder diffraction pattern with characteristic peaks expressed in values of degrees 2Θ at about 5.24, about 7.53, about 11.40, about 15.04, about 19.54, about 22.18, and about 25.90±0.2.

In another embodiment of the invention the crystalline meglumine salt of Formula (I) is a monohydrate having an X-ray powder diffraction pattern with characteristic peaks expressed in values of degrees 2Θ at about 7.53, about 11.40, about 19.54, and about 25.90±0.2.

In another aspect of the invention the crystalline meglumine salt of Formula (I) is anhydrous and has an X-ray powder diffraction pattern with characteristic peaks expressed in values of degrees 2Θ at about 7.21, about 11.23, about 13.36, about 20.19, about 24.92, and about 27.33±0.2.

In an embodiment of the invention the crystalline meglumine salt of Formula (I) is anhydrous and has an X-ray powder diffraction pattern with characteristic peaks expressed in values of degrees 2Θ at about 7.21, about 13.36, about 24.92, and about 27.33±0.2.

In another aspect, the invention comprises administering a meglumine salt of a Formula I thienopyrimidine compound to a mammal, such as a mammal suffering from or susceptible to heart failure.

DETAILED DESCRIPTION

Definitions

Figure 1:
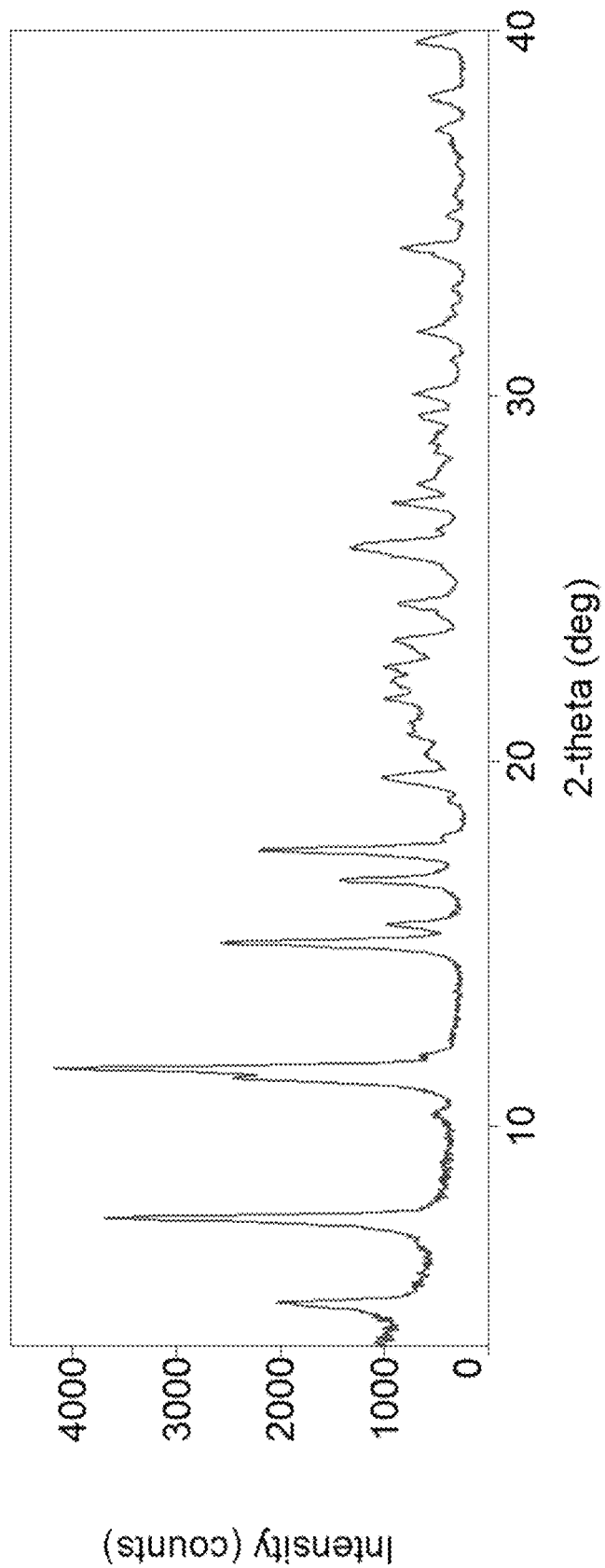
FIG. 1 shows the XRPD pattern of the monohydrate meglumine salt of 2-(3,4-dichlorobenzyl)-5-methyl-4-oxo-3,4-dihydrothieno[2,3-d]pyrimidine-6-carboxylate.

As used herein, and unless noted to the contrary, the following terms and phrases have the meaning noted below.

"Amino" refers to the —NH$_2$ substituent.

"Carboxyl" refers to the —CO$_2$H substituent.

"Carbonyl" refers to a —C(O)—, —(CO)— or —C(=O)— group. All notations are used interchangeably within the specification.

"Cyano" refers to the —C≡N substituent.

"Acetyl" refers to the —C(O)CH$_3$ substituent.

"Hydroxy" or "hydroxyl" refers to the —OH substituent.

"Oxo" refers to a =O substituent.

"Thio" or "thiol" refer to a —SH substituent.

"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_8$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like.

"Lower alkyl" has the same meaning as alkyl defined above but having from one to four carbon atoms ($C_1$-$C_4$ alkyl).

"Alkenyl" refers to an unsaturated alkyl group having at least one double bond and from two to twelve carbon atoms ($C_2$-$C_{12}$ alkenyl), from two to eight carbon atoms ($C_2$-$C_8$ alkenyl) or from two to six carbon atoms ($C_2$-$C_6$ alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms ($C_2$-$C_{12}$ alkynyl), from two to ten carbon atoms ($C_2$-$C_{10}$ alkynyl) from two to eight carbon atoms ($C_2$-$C_8$ alkynyl) or from two to six carbon atoms ($C_2$-$C_6$ alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkoxy" refers to a radical of the formula —OR$_a$ where R$_a$ is an alkyl having the indicated number of carbon atoms as defined above. Examples of alkoxy groups include without limitation —O-methyl (methoxy), —O-ethyl (ethoxy), —O-propyl (propoxy), —O-isopropyl (iso propoxy) and the like.

"Aryl" or "aryl group" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to an aryl group or a substituted aryl group.

"Cycloalkyl" or "cycloalkyl ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo [2.2.1]heptanyl, and the like.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl", heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

"Meglumine" refers to the structure

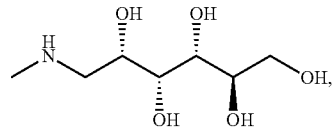

also referred to as (2R,3R,4R,5S)-6-(methylamino) hexane-1,2,3,4,5-pentol.

"Sulfoxide" refers to a —S(O)— group in which the sulfur atom is covalently attached to two carbon atoms.

"Sulfone" refers to a —S(O)$_2$— or —(SO$_2$)— group in which a hexavalent sulfur is attached to each of the two oxygen atoms through double bonds and is further attached to two carbon atoms through single covalent bonds.

The compound of the invention can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

An example of a tautomer of the present application is as follows:

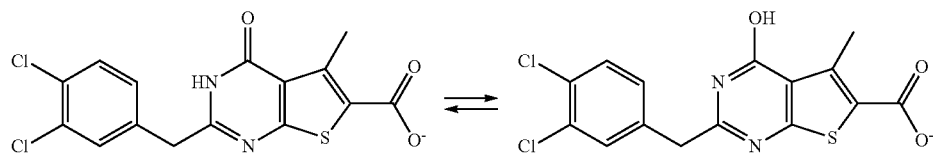 [SMILES: Cc1c(C(=O)[O-])sc2nc(Cc3ccc(Cl)c(Cl)c3)[nH]c(=O)c12 ; Cc1c(C(=O)[O-])sc2nc(Cc3ccc(Cl)c(Cl)c3)nc(O)c12]

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease. In the context of the present invention the terms "treat", "treating" and "treatment" also refer to:
(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "effective amount" refers to an amount of a compound of the invention or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy or synergies with another therapeutic agent.

The terms "modulate", "modulation" and the like refer to the ability of a compound to increase or decrease the function, or activity of, for example, phosphodiesterase 9 (PDE9). "Modulation", in its various forms, is intended to encompass inhibition, antagonism, partial antagonism, activation, agonism and/or partial agonism of the activity associated with cGMP levels. PDE9 inhibitors are compounds that bind to, partially or totally block stimulation, decrease, prevent, delay activation, inactivate, desensitize, or down regulate signal transduction. The ability of a compound to modulate kinase activity can be demonstrated in an enzymatic assay or a cell-based assay.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human) In one embodiment, a patient is a human, such as a human infant, child, adolescent or adult.

Therapeutic Use

In certain aspects, the mammal being treated is suffering from or has suffered from heart failure. The mammal also may be suffering from or has suffered from congestive heart failure. The mammal also may be suffering from or has suffered from cardiogenic shock.

In particular embodiments, the mammal being treated is suffering from or susceptible to a cardiovascular disease or condition, including cardiac hypertrophy, heart failure with preserved ejection fraction (HfpEF), heart failure with reduced ejection fraction (HFrEF) (reduced systolic function), reduced diastolic function, maladaptive hypertrophy, heart failure with preserved systolic function, diastolic heart failure, hypertensive heart disease, aortic stenosis, hypertrophic cardiomyopathy, and/or post ischemic cardiac remodeling.

In a preferred aspect, a mammal that is suffering from or has suffered from heart failure is selected for heart failure treatment and a salt of a compound as disclosed herein is administered to the selected mammal. The mammal may be identified as exhibiting congestive heart failure disorder having low cardiac output and/or low stroke volume.

In preferred aspects, the treated mammal is a human.

A thienopyrimidine salt can be administered in conjunction with one or more other agents distinct for treating heart failure.

Kits are also provided that suitably may comprise a thienopyrimidine salt as disclosed herein and instructions for use of the thienopyrimidine salt for treating heart failure. The instructions typically will be in written form, for example as presented on a package insert or a product label.

Use of a thienopyrimidine salt as disclosed herein can provide an increase in measured cyclic GMP levels, for example an increase of 20, 30, 40, 50, 80 or 100 percent or more measured cyclic GMP value in a subject's blood or urine sample relative to a control (blood or urine sample from the subject prior to treatment with a thienopyrimidine salt as disclosed herein.

The subject to be administered with one or more thienopyrimidine salts as disclosed herein is suitably a mammal, or particularly a human. In some embodiments, the method of treating heart failure may further comprise a step of selecting the subject suffering from or susceptible to heart failure, including a subject that has suffered from or is susceptible to congestive heart failure of acute cardiogenic shock.

In additional embodiments, the method of treating heart failure may further comprise a step of selecting the subject suffering from or susceptible to cardiac hypertrophy, heart failure with preserved ejection fraction (HfpEF), heart failure with reduced ejection fraction (HFrEF) (reduced systolic function), reduced diastolic function, maladaptive hypertrophy, heart failure with preserved systolic function, diastolic heart failure, hypertensive heart disease, aortic stenosis, hypertrophic cardiomyopathy, and/or post ischemic cardiac remodeling.

In some embodiments, one or more thienopyrimidine salts as disclosed herein may be administered in combination with one or more additional distinct heart failure therapeutic agents. Exemplary agents for co-administration include Angiotensin-Converting Enzyme (ACE) Inhibitors such as Captopril (Capoten), Enalapril (Vasotec), Fosinopril (Monopril), Lisinopril (Prinivil, Zestril), Perindopril (Aceon), Quinapril (Accupril), Ramipril (Altace) and Trandolapril (Mavik); Angiotensin II Receptor Blockers (or Inhibitors) such as Candesartan (Atacand), Losartan (Cozaar), and Valsartan (Diovan); Neprilysin inhibitors alone or in combinations, such as Angiotensin-Receptor Neprilysin Inhibitors (ARNIs) combinations like sacubitril/valsartan (Entresto), $I_f$ Channel Blocker (or inhibitor) such as Ivabradine (Corlanor); Beta Blockers such as Bisoprolol (Zebeta), Metoprolol succinate (Toprol XL), Carvedilol (Coreg), and Carvedilol CR (Coreg CR)Toprol XL; Aldosterone Antagonists such as Spironolactone (Aldactone), and Eplerenone (Inspra); Hydralazine and isosorbide dinitrate; Diuretics such as Furosemide (Lasix), Bumetanide (Bumex), Torsemide (Demadex), Chlorothiazide (Diuril), Amiloride (Midamor Chlorthalidone (Hygroton), Hydro-chlorothiazide (Esidrix, Hydrodiuril), Indapamide (Lozol), Metolazone (Zaroxolyn) and Triamterene (Dyrenium); Anticoagulants (blood thinners); and/or Cholesterol lowering drugs (statins).

Therapeutically effective dosages of a thienopyrimidine salt as disclosed herein may vary rather widely and may be adjusted or selected to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Suitable effective dosages may range from 0.01 to 5 or 10 mg/kg per day, although dosages outside such ranges also may be utilized as appropriate.

The therapeutically effective dose of the salt can be administered to the subject by a variety of administration routes. Oral or topical administration will be typically preferred although other administration protocols also may be utilized as parenteral, sublingual, or via an implanted reservoir. In some embodiments, the salt may be formulated for administering purposes in a capsule, a tablet, a gel, a powder, liquid, suspension or emulsion.

As discussed, therapeutic compositions are also provided that include one or more salts as disclosed herein optionally with a pharmaceutically acceptable carrier.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a salt of the compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the salt useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

In one preferred aspect, the salt may be formulated for administering purposes in a capsule, a tablet, a gel, a powder, liquid, suspension or emulsion; however, the administering methods may not be particularly limited.

In some embodiments, the therapeutically effective dose of the salt of the compound may be administered orally, parenterally, buccal, sublingually, or via an implanted reservoir The salt of the compound(s) can be included in a kit, container, pack, or dispenser together with instructions for administration. For instance, the kit may contain a product label or written package insert that discloses use of the composition for treating including prophylaxis of heart failure.

Preferred salts of the invention may be potent inhibitors of phosphodiesterase 9 (PDE9) as determined by in vitro assay.

The following non-limiting examples are illustrative of the invention.

Example 1

Thienopyrimidine salts for use in the present methods and kits can be synthesized by known procedures, including those procedures disclosed in U.S. Pat. No. 8,293,754 to Gotanda et al. Thienopyrimidines can be synthesized by annulation of the pyrimidine nucleus on the parent thiophene ring or annulation of a thiophene nucleus on the parent pyrimidine ring. See Abdel-Megid et al., *J. Pharm. Appl Chem.*, 2, No. 3, 103-127 (2016).

Synthesis of 2-(3,4-dichlorobenzyl)-5-methyl-4-oxo-3,4-dihydrothieno[2,3-d]pyrimidine-6-carboxylate (1). A mixture of 1 mmol of ethyl 2,5-dimethyl-4-oxo-3,4-dihydrothieno[2,3-d]pyrimidine-6-carboxylate (2), 1 mmol of sodium carbonate, 15 mL of acetonitrile and 1 mL of the appropriate benzyl chloride were combined and heated under reflux overnight. The volatiles were removed in vacuo and the resulting residue was purified by column chromatography over silica gel (eluted with chloroform:methanol=100:1) to afford 45% of the ethyl 2-(3,4-dichlorobenzyl)-5-methyl-4-oxo-3,4-dihydrothieno[2,3-d]pyrimidine-6-carboxylate (3).

The resulting thienopyrimidine carboxylate was combined with 3.4 mL of a 1N aqueous sodium hydroxide solution and 2.2 mL of ethanol and heated under reflux for 2 hours. Once cooled, the reaction liquid was poured over ice, rendered acidic with diluted hydrochloric acid, where the subsequently precipitated crystals were recovered by filtration. After washing with water, the crystals were dried by heating under reduced pressure to afford the desired carboxylic acid (1). (see U.S. Pat. No. 8,293,754, Example 1)

Example 2

Synthesis of meglumine 2-(3,4-dichlorobenzyl)-5-methyl-4-oxo-3,4-dihydrothieno[2,3-d]pyrimidine-6-carboxylate monohydrate (4). A 1.0 equivalent portion (450 mg) of 2-(3,4-dichlorobenzyl)-5-methyl-4-oxo-3,4-dihydrothieno[2,3-d]pyrimidine-6-carboxylic acid (1) was combined with 14 volumes absolute ethanol and a 10% aqueous solution of meglumine to form an initial slurry. The combined mixture was slurried at 45° C. where a thin slurry initially formed. The thin slurry gradually turned into an unstirrable slurry. The resulting slurry was diluted with additional volumes of EtOH:Water (8:2 vol) which afforded a total solvent volume of 35-45 volumes. The slurry was filtered and washed with twice with 2-portion volumes of EtOH:water (8:2 vol) to afford the desired salt (4). See FIG. 1 and Table 1.

TABLE 1

XRPD peak table for meglumine salt monohydrate form

| 2θ (deg) | d-spacing (Å) | Relative intensity (a.u) |
|---|---|---|
| 5.24 | 16.86 | 55.61 |
| 7.53 | 11.73 | 74.75 |
| 10.33 | 8.55 | 2.10 |
| 11.40 | 7.75 | 100.00 |
| 11.62 | 7.61 | 41.66 |
| 15.04 | 5.89 | 51.16 |
| 15.55 | 5.69 | 20.19 |
| 16.77 | 5.28 | 48.02 |
| 17.58 | 5.04 | 47.52 |
| 19.54 | 4.54 | 53.15 |
| 20.16 | 4.40 | 12.22 |
| 21.00 | 4.23 | 15.53 |
| 21.75 | 4.08 | 3.41 |
| 22.18 | 4.00 | 42.48 |
| 23.33 | 3.81 | 30.10 |
| 24.38 | 3.65 | 33.13 |
| 25.90 | 3.44 | 83.34 |
| 27.05 | 3.29 | 11.70 |
| 27.62 | 3.23 | 26.76 |
| 28.67 | 3.11 | 31.24 |
| 29.46 | 3.03 | 18.48 |
| 30.05 | 2.97 | 21.65 |

TABLE 1-continued

XRPD peak table for meglumine salt monohydrate form

| 2θ (deg) | d-spacing (Å) | Relative intensity (a.u) |
|---|---|---|
| 31.82 | 2.81 | 25.72 |
| 34.03 | 2.63 | 13.42 |
| 37.32 | 2.41 | 12.64 |
| 38.18 | 2.36 | 10.31 |
| 39.72 | 2.27 | 8.62 |

Example 3

Figure 2:
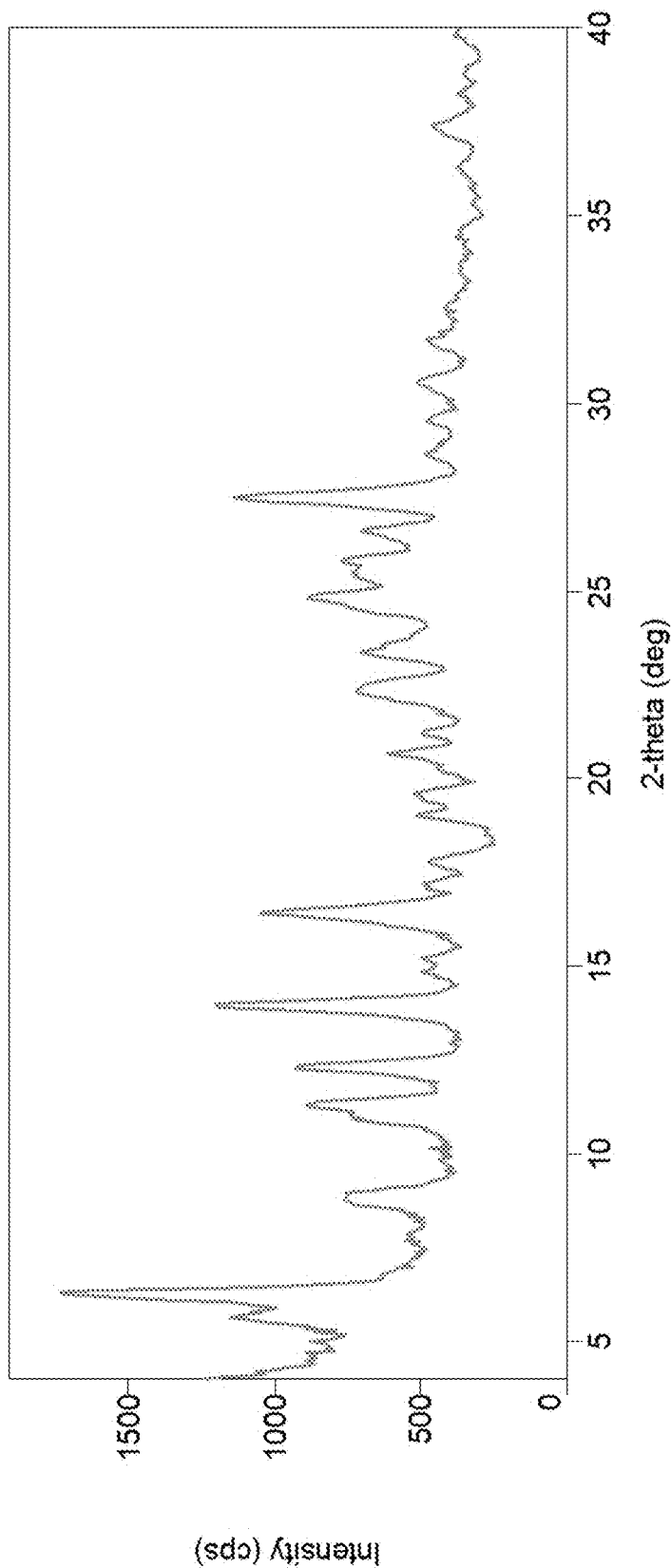
FIG. 2 shows the XRPD of the anhydrous meglumine salt of 2-(3,4-dichlorobenzyl)-5-methyl-4-oxo-3,4-dihydrothieno[2,3-d]pyrimidine-6-carboxylate.

Synthesis of anhydrous meglumine 2-(3,4-dichlorobenzyl)-5-methyl-4-oxo-3,4-dihydrothieno[2,3-d]pyrimidine-6-carboxylate (5). A 1.0 equivalent portion (450 mg) of 2-(3,4-dichlorobenzyl)-5-methyl-4-oxo-3,4-dihydrothieno[2,3-d]pyrimidine-6-carboxylic acid (1) was combined with anhydrous tetrahydrofuran (THF) and a 10% aqueous solution of meglumine (426.0 µL) to form an almost clear solution. The combined mixture was slurried at room temperature and gradually turned into a thick slurry. The resulting slurry was diluted with additional volumes of anhydrous THF to afford the desired anhydrous salt (5). See FIG. 2 and Table 2.

TABLE 2

XRPD peak table for meglumine salt anhydrous crystalline form

| 2θ (deg) | d-spacing (Å) | Relative intensity (a.u) |
|---|---|---|
| 7.21 | 12.26 | 100.00 |
| 11.23 | 7.87 | 43.69 |
| 13.36 | 6.62 | 60.24 |
| 14.49 | 6.11 | 33.30 |
| 17.05 | 5.20 | 15.35 |
| 17.81 | 4.98 | 32.83 |
| 20.19 | 4.39 | 43.14 |
| 21.78 | 4.08 | 37.40 |
| 22.42 | 3.96 | 36.42 |
| 23.03 | 3.86 | 28.72 |
| 24.92 | 3.57 | 50.81 |
| 25.47 | 3.49 | 13.88 |
| 27.33 | 3.26 | 72.55 |
| 29.15 | 3.06 | 12.73 |
| 34.68 | 2.58 | 8.49 |
| 36.20 | 2.48 | 6.39 |

Example 4

Synthesis of anhydrous meglumine 2-(3,4-dichlorobenzyl)-5-methyl-4-oxo-3,4-dihydrothieno[2,3-d]pyrimidine-6-carboxylate "Form D" (6). A 1.0 equivalent portion (450 mg) of 2-(3,4-dichlorobenzyl)-5-methyl-4-oxo-3,4-dihydrothieno[2,3-d]pyrimidine-6-carboxylic acid (1) was combined with anhydrous tetrahydrofuran (THF) and a 10% aqueous solution of meglumine (426.0 µL) to form an almost clear solution. The combined mixture was slurried at room temperature and gradually turned into a thick slurry. The resulting slurry was diluted with additional volumes of ethanol/water (8:2 v/v %) to provide the monohydrate salt (4). The monohydrate salt, also referred to as the "hydrate", was heated to 170° C. and held at 170° C. for 30 min then cooled to room temperature (20-23° C.) to afford the dehydrated salt (6) identified as "Form D". See Table 3.

TABLE 3

XRPD of anhydrous meglumine carboxylate "Form D"

| 2θ (deg) | d-spacing (Å) | Relative intensity (a.u) |
|---|---|---|
| 7.43 | 11.88 | 85.43 |
| 8.17 | 10.81 | 20.49 |
| 8.90 | 9.93 | 19.48 |
| 10.60 | 8.34 | 6.06 |
| 11.56 | 7.65 | 62.68 |
| 12.37 | 7.15 | 30.73 |
| 13.83 | 6.40 | 27.90 |
| 15.03 | 5.89 | 100.00 |
| 15.73 | 5.63 | 46.79 |
| 16.34 | 5.42 | 25.55 |
| 17.44 | 5.08 | 63.61 |
| 19.29 | 4.60 | 15.81 |
| 20.40 | 4.35 | 24.12 |
| 21.26 | 4.18 | 15.03 |
| 21.69 | 4.09 | 7.95 |
| 22.28 | 3.99 | 39.22 |
| 24.43 | 3.64 | 7.18 |
| 25.26 | 3.52 | 62.14 |
| 26.44 | 3.37 | 22.11 |
| 26.89 | 3.31 | 20.77 |
| 27.89 | 3.20 | 3.26 |
| 29.09 | 3.07 | 9.53 |
| 29.76 | 3.00 | 13.94 |
| 30.69 | 2.91 | 3.25 |
| 32.01 | 2.79 | 4.25 |
| 34.99 | 2.56 | 22.56 |
| 37.51 | 2.40 | 3.52 |
| 38.47 | 2.34 | 18.83 |

Example 5

Synthesis of anhydrous meglumine 2-(3,4-dichlorobenzyl)-5-methyl-4-oxo-3,4-dihydrothieno[2,3-d]pyrimidine-6-carboxylate "Form O" (7). A 1.0 equivalent portion (450 mg) of 2-(3,4-dichlorobenzyl)-5-methyl-4-oxo-3,4-dihydrothieno[2,3-d]pyrimidine-6-carboxylic acid (1) was combined with a DMSO:acetonitrile (1:1 v/v) solvent system and a 10% aqueous solution of meglumine which was "crash cooled" to quickly form a solvate form of the crystals. The resulting crystals were recovered and dried at atmosphere to afford "Form O" of the desired anhydrous salt (7). See Table 4.

TABLE 4

XRPD of anhydrous meglumine carboxylate "Form O"

| 2θ (deg.) | d-spacing (Å) | Relative intensity (a.u) |
|---|---|---|
| 9.42 | 9.38 | 66.59 |
| 10.32 | 8.57 | 47.56 |
| 12.16 | 7.27 | 29.73 |
| 15.18 | 5.83 | 100.00 |
| 17.19 | 5.15 | 28.94 |
| 18.40 | 4.82 | 23.86 |
| 19.44 | 4.56 | 15.21 |
| 20.83 | 4.26 | 20.85 |
| 21.45 | 4.14 | 32.13 |
| 22.27 | 3.99 | 45.58 |
| 22.56 | 3.94 | 8.54 |
| 23.21 | 3.83 | 26.28 |
| 23.66 | 3.76 | 14.46 |
| 24.09 | 3.69 | 5.44 |
| 25.50 | 3.49 | 13.25 |
| 26.76 | 3.33 | 13.81 |
| 27.34 | 3.26 | 26.41 |
| 29.16 | 3.06 | 11.42 |
| 30.77 | 2.90 | 5.15 |
| 32.58 | 2.75 | 5.97 |
| 34.22 | 2.62 | 11.47 |
| 39.11 | 2.30 | 4.17 |

Example 6

Synthesis of arginine 2-(3,4-dichlorobenzyl)-5-methyl-4-oxo-3,4-dihydrothieno[2,3-d]pyrimidine-6-carboxylate (8). A 1.0 equivalent portion (450 mg) of 2-(3,4-dichlorobenzyl)-5-methyl-4-oxo-3,4-dihydrothieno[2,3-d]pyrimidine-6-carboxylic acid (1) was combined with an ethanol:water (8:2 v/v) solvent system and a 1.1 equivalent portion of L-arginine. The combined mixture was slurried at room temperature and gradually turned into a thick slurry. The resulting slurry was diluted with additional volumes of ethanol/water (8:2 v/v %)(total of 35-40 volumes). The crystals were recovered and dried to afford the desired arginine salt (8).

Example 7

Synthesis of lysine 2-(3,4-dichlorobenzyl)-5-methyl-4-oxo-3,4-dihydrothieno[2,3-d]pyrimidine-6-carboxylate (9). A 1.0 equivalent portion (450 mg) of 2-(3,4-dichlorobenzyl)-5-methyl-4-oxo-3,4-dihydrothieno[2,3-d]pyrimidine-6-carboxylic acid (1) was combined with an ethanol:water (8:2 v/v) solvent system and a 1.1 equivalent portion of L-lysine. The combined mixture was slurried at room temperature and gradually turned into a thick slurry. The resulting slurry was diluted with additional volumes of ethanol/water (8:2 v/v %). The crystals were recovered and dried to afford the desired lysine salt (9).

Example 8

Initial studies identified thienopyrimidine carboxylic acids as PDE9 inhibitors which could be used to treat or prevent HF. However, the carboxylic acid form of the compounds proved to be almost completely insoluble in any pharmaceutically acceptable formulation. In further studies, the potassium salt was identified as a candidate for formulation because it was soluble, provided high exposure in preclinical toxicology studies, and was relatively easy to scale up. However, the sodium and potassium salt forms of the thienopyrimidines demonstrate many insurmountable challenges such as solid form instability, high hygroscopicity, numerous polymorphs, and high residual solvent retention. Unexpectedly the monohydrate crystalline meglumine salt of the thienopyrimidine compounds afforded the desired properties for a pharmaceutical formulation, as shown in Table 5.

TABLE 5

Crystalline Salts of Thienopyrimidine Carboxylates (1)

| Property | Meglumine Monohydrate (4) | L-Arginine Monodyrate (8) | L-Lysine Monohydrate (9) | Potassium |
|---|---|---|---|---|
| Stability | | | | |
| Drying under vaccum @50 for 36 hrs | Form remains unchanged | Form changes | Form changes | Form changes |
| Hygroscopicity | | | | |
| DVS[†] weight gain | 0.7% | 5.9% | 6.4% | 8-22.5% |

[†]Dynamic Vapor Sorption @ 25° C./95% RH

As shown in Table 5 the meglumine salt (4) exhibits both low hygroscopicity and form stability as compared to the L-arginine (8), L-lysine (9) and potassium salts.

Example 9: Dog Pharmacokinetic Study

Healthy dogs were used to study different salt candidates to evaluate the pharmacokinetic profile of each candidate. Six treatment arms were employed:

| N = 4 animals/arm | Formulation |
|---|---|
| Arms 1-4 | K+, L-Arginine, L-Lysine, Meglumine dosed as powder in capsule |
| Arm 5 | Solution of carboxylic acid form in 80% propylene glycol (PG)/20% water with 54 mM NaOH |
| Arm 6 | Solution of K+ salt in 0.5% methyl cellulose (MC) |

Animals were fasted overnight with free access to water. Pentagastrin (PG) (6 μg/kg, IM) was administered 30 min prior to dosing. Food was resumed 4 h post dose.

The mean plasma concentration-time profiles of the salt candidates, free acid, and controls provided the following results:

TABLE 6

Pharmacokinetic Profile

| Salt/Free Acid | $AUC_{last}$ (ng * hr/mL) | $C_{max}$ (ng/mL) | $T_{max}$ (hr) |
|---|---|---|---|
| Meglumine salt (monohydrate) | 1008 | 280 | 1.13 |
| L-Arginine salt (monohydrate) | 705 | 246 | 1.38 |
| L-Lysine salt (monohydrate) | 495 | 78.4 | 3.50 |
| Potassium Salt (powder in capsule) | 966 | 398 | 1.25 |
| Free Acid (Arm 5 formulation) | 972 | 314 | 0.56 |
| Potassium Salt (Arm 6 formulation) | 1336 | 422 | 0.79 |

In Table 6 the meglumine salt (4) demonstrates a superior pharmacokinetic profile while retaining the excellent form and stability properties shown in Table 5. The data show that meglumine salt dosed as powder in a capsule (PIC) provided comparable exposure to the free acid and potassium salt dosed as solutions, respectively. The results of the meglumine salt (4) are superior to that of the L-arginine (8), L-lysine (9), and the potassium salt (PIC) with regard to the $AUC_{last}$, $C_{max}$, and $T_{max}$ values. Similarly, the $AUC_{last}$ of the monohydrate meglumine salt shows a comparable rate of elimination to that of the free acid. Therefore, the pharmacokinetic data demonstrates that the monohydrate meglumine salt is superior to the other salt derivatives and has a comparable bioavailability to the free acid.

All documents mentioned herein are herein incorporated by reference herein in their entirety.

What is claimed is:

1. A salt according to Formula (I) having the structure:

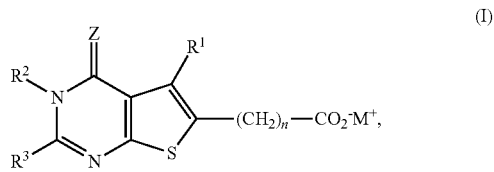

(I)

or stereoisomers, tautomers or hydrates thereof,
wherein:
$R^1$ is hydrogen, $(C_1-C_6)$alkyl, $(C_1-C_6)$alkoxy or $(C_1-C_6)$ haloalkyl containing 1-6 halogen atoms;
$R^2$ is hydrogen, $(C_1-C_6)$alkyl, $[(C_1-C_6)$alkylene]aryl or amino;
$R^3$ is hydrogen, $(C_1-C_6)$alkyl, $(C_2-C_6)$alkenyl, $[(C_1-C_6)$alkylene]N$(R^4)(R^5)$, $[(C_1-C_6)$alkylene]S$(R^4)$ or —X—Y, or $R^2$ and $R^3$ together with the atoms to which they are attached form a heterocyclyl;
$R^4$ and $R^5$ are independently H or $(C_1-C_6)$alkyl;
X is a chemical bond, —$CH_2$—, —CH(OH)—, —CH($C_6H_5$)—, —CO—, —$CH_2CH_2$—, $CH_2CO$—, —$COCH_2$—, S, O or NH;
Y is cycloalkyl, heterocyclyl, aryl or heteroaryl;
Z is S or O;
n is 0, 1, 2, 3 or 4;
$M^+$ is

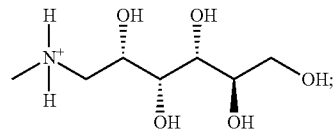

and
wherein any alkyl, alkylene, cycloalkyl, heterocyclyl, heteroaryl or aryl is optionally substituted with 1, 2 or 3 groups selected from OH, CN, halogen, $(C_1-C_6)$alkyl, $O(C_1-C_6)$ alkyl, $(C_2-C_6)$alkenyl, haloalkyl, amino, oxo and nitro.

2. The salt, or stereoisomers, tautomers or hydrates thereof according to claim 1, wherein $R^1$ is $(C_1-C_6)$alkyl, $R^2$ is —H and $R^3$ is —X—Y.

3. The salt, or stereoisomers, tautomers or hydrates thereof according to claim 2, wherein X is —$CH_2$— and Y is an aryl group.

4. The salt, or stereoisomers, tautomers or hydrates thereof according to claim 3, wherein X is —$CH_2$— and Y is $(C_1-C_6)$aryl substituted by one more halogen atoms.

5. The salt, or stereoisomers, tautomers or hydrates thereof according to claim 2, wherein Z is oxygen.

6. The salt, or stereoisomers, tautomers or hydrates thereof according to claim 1, wherein n is 0.

7. The salt, or stereoisomers, tautomers or hydrates thereof according to claim 1, having the structure:

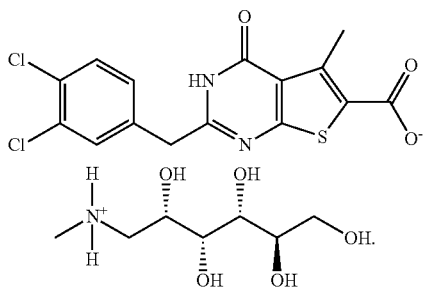

8. The salt, or stereoisomers, tautomers or hydrates thereof according to claim 1, wherein the meglumine salts of Formula (I) are crystalline solids.

9. The salt, or stereoisomers, tautomers or hydrates thereof according to claim 8, wherein the crystalline solids of Formula (I) are a monohydrate.

10. The salt according to claim 8, wherein the crystalline solids of Formula (I) are anhydrous.

11. A crystalline solid of a salt, or stereoisomers, tautomers or hydrates thereof having the structure:

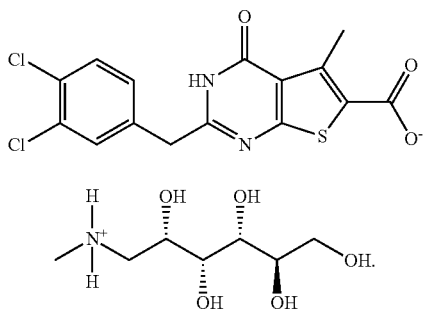

12. The salt, stereoisomers, tautomers, or hydrates thereof according to claim 11, having an X-ray powder diffraction pattern with characteristic peaks expressed in values of degrees 2Θ at about 5.24, about 7.53, about 11.40, about 11.62, about 15.04, about 16.77, about 17.58, about 19.54, about 22.18, about 23.33, about 24.38, about 25.90 and about 28.67±0.2.

13. The salt, stereoisomers, tautomers or hydrates thereof according to claim 11, having an X-ray powder diffraction pattern with characteristic peaks expressed in values of degrees 2Θ at about 5.24, about 7.53, about 11.40, about 15.04, about 19.54, about 22.18, and about 25.90±0.2.

14. The salt, stereoisomers, tautomers, or hydrates thereof according to claim 11, having an X-ray powder diffraction pattern with characteristic peaks expressed in values of degrees 2Θ at about 7.53, about 11.40, about 19.54, and about 25.90±0.2.

15. The salt, stereoisomers, tautomers, or hydrates thereof according to claim 11, having an X-ray powder diffraction pattern according to FIG. 1.

16. A method of treating a cardiovascular disease or condition in a mammal in need thereof comprising administering to the mammal a therapeutically effective amount of a salt of a compound according to Formula (I):

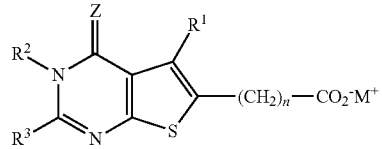

or stereoisomers, tautomers or hydrates thereof, wherein:

$R^1$ is hydrogen, $(C_1\text{-}C_6)$alkyl, $(C_1\text{-}C_6)$alkoxy or $(C_1\text{-}C_6)$haloalkyl containing 1-6 halogen atoms;

$R^2$ is hydrogen, $(C_1\text{-}C_6)$alkyl, $[(C_1\text{-}C_6)\text{alkylene}]$aryl or amino;

$R^3$ is hydrogen, $(C_1\text{-}C_6)$alkyl, $(C_2\text{-}C_6)$alkenyl, $[(C_1\text{-}C_6)\text{alkylene}]N(R^4)(R^5)$, $[(C_1\text{-}C_6)\text{alkylene}]S(R^4)$ or —X—Y, or $R^2$ and $R^3$ together with the atoms to which they are attached form a heterocyclyl;

$R^4$ and $R^5$ are independently H or $(C_1\text{-}C_6)$alkyl;

X is a chemical bond, —$CH_2$—, —CH(OH)—, —CH$(C_6H_5)$—, —CO—, —$CH_2CH_2$—, $CH_2CO$—, —$COCH_2$—, S, O or NH;

Y is cycloalkyl, heterocyclyl, aryl or heteroaryl;

Z is S or O;

n is 0, 1, 2, 3 or 4;

$M^+$ is

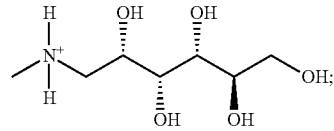

and wherein any alkyl, alkylene, cycloalkyl, heterocyclyl, heteroaryl or aryl is optionally substituted with 1, 2 or 3 groups selected from OH, CN, halogen, $(C_1\text{-}C_6)$alkyl, $O(C_1\text{-}C_6)$alkyl, $(C_2\text{-}C_6)$alkenyl, haloalkyl, amino, oxo and nitro.

17. The method of claim 16, wherein the meglumine salt, or stereoisomers, tautomers or hydrates thereof, according to Formula (I) is:

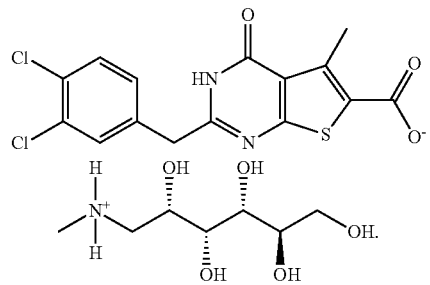

18. The method of claim 17, wherein the meglumine salt, or stereoisomers, tautomers or hydrates thereof, according to Formula (I) is the crystalline monohydrate form of:

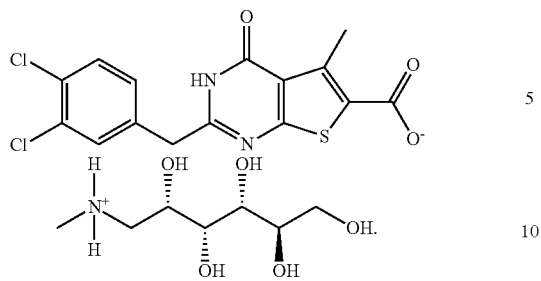

19. The method of claim 18, wherein the meglumine salt, or stereoisomers, tautomers or hydrates thereof, has an X-ray powder diffraction pattern according to FIG. 1.

20. The method of claim 16, wherein the cardiovascular disease or condition is cardiac hypertrophy, heart failure, heart failure with preserved ejection fraction (HfpEF), heart failure with reduced ejection fraction (HFrEF) (reduced systolic function), reduced diastolic function, maladaptive hypertrophy, heart failure with preserved systolic function, diastolic heart failure, hypertensive heart disease, aortic stenosis, hypertrophic cardiomyopathy, or post ischemic cardiac remodeling.

21. The method of claim 20, wherein the cardiovascular disease or condition is heart failure.

\* \* \* \* \*